United States Patent
Zetterlund

(10) Patent No.: US 7,206,374 B2
(45) Date of Patent: Apr. 17, 2007

(54) METHOD AND APPARATUS TO GENERATE AN X-RAY IMAGE OF THE FEMALE BREAST

(75) Inventor: Lennart Zetterlund, Bro (SE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 11/064,468

(22) Filed: Feb. 23, 2005

(65) Prior Publication Data

US 2005/0195938 A1 Sep. 8, 2005

(30) Foreign Application Priority Data

Feb. 23, 2004 (DE) .................... 10 2004 008 735

(51) Int. Cl.
*A61B 6/04* (2006.01)
(52) U.S. Cl. .................................. 378/37; 378/62
(58) Field of Classification Search .............. 378/37, 378/62, 98.11, 108, 147, 205, 207
See application file for complete search history.

(56) References Cited

U.S. PATENT DOCUMENTS

| | | | |
|---|---|---|---|
| 6,480,565 B1 * | 11/2002 | Ning | 378/37 |
| 2003/0194051 A1 | 10/2003 | Wang et al. | |
| 2004/0101095 A1 * | 5/2004 | Jing et al. | 378/37 |

FOREIGN PATENT DOCUMENTS

EP 0 432 119 11/1995

* cited by examiner

*Primary Examiner*—Edward Glick
*Assistant Examiner*—Hoon Song
(74) *Attorney, Agent, or Firm*—Schiff Hardin LLP

(57) ABSTRACT

In a method and an apparatus to generate an x-ray image of the female breast, a digital image transducer is used as the x-ray receiver. In a first time segment, an exposure ensues of the entire reception area of the x-ray receiver with an x-ray beam, at least until a point in time at which the position and size of the breast are detectable in the x-ray image. Subsequently, in a second time segment the x-ray beam is limited to a partial beam that irradiates only a sub-area of the reception area containing the breast, or a part of the breast, and the irradiation is continued only with this partial beam.

8 Claims, 1 Drawing Sheet

METHOD AND APPARATUS TO GENERATE AN X-RAY IMAGE OF THE FEMALE BREAST

BACKGROUND OF THE INVENTION

1. Field of the Invention

The invention concerns a method and an apparatus for generation of an x-ray image of the female breast.

2. Description of the Prior Art

In x-ray mammography, a two-dimensional x-ray image of the female breast is generated. During the x-ray image acquisition, the breast is located between two compression plates, of which the compression plate associated with an x-ray source is permeable for the x-ray radiation that is used. A planar x-ray receiver, for example an x-ray film or a digital image transducer device, is located on the opposite compression plate. The x-ray beam used in the exposure, originating approximately from a point, is dimensioned such that it irradiates the entire reception surface of the x-ray receiver. The tissue appearing light on the x-ray image is then completely surrounded by an over-exposed (i.e. dark) area, and the evaluation of the x-ray image is made easier. However, this has the consequence that not only the breast but also the surrounding tissue recorded by the x-ray beam are irradiated. This does not lead directly to an increased radiation exposure of the breast; however, due to scattering on the compression plates, x-ray radiation is generated that can both disadvantageously influence the image quality and indirectly lead to an increased radiation exposure of the patient or the operating personnel. Given the use of an x-ray film as an x-ray receiver, the size of the film (and thus the necessary cross-sectional area of the x-ray beam) can be simply adapted to the current anatomical conditions by selection of a matching film format. This is not possible in x-ray mammography apparatuses in which a relatively costly digital image transducer device is used as the x-ray receiver, such that the entire reception surface of the x-ray receiver is exposed when the dimensions of the breast located between the compression plates are significantly smaller than the dimensions of the reception surface (and thus of the x-ray beam used).

SUMMARY OF THE INVENTION

An object of the present invention is to provide a method for generation of an x-ray image of the female breast that leads to a reduction of the radiation exposure in the surroundings without a quality loss in the x-ray image. A further object of the invention is to provide a device to implement the method.

With regard to the method, this object is achieved by a method wherein digital image transducer is used as the x-ray receiver, and wherein irradiation of the entire reception area of the x-ray receiver ensues in a first time segment with an x-ray beam, at least up to a point in time in which the position and size of the breast are detectable. In a second, subsequent time segment, the x-ray beam is limited to a partial beam that irradiates only a sub-area of the reception area containing the breast or a part of the breast, and the irradiation proceeds exclusively using this partial beam.

By these measures it is ensured that the x-ray radiation is limited to an area or a solid angle that is necessary for a diagnostic evaluation of the x-ray image, such that the scatter radiation created (and thus the radiation exposure of other people or other body parts) in the surroundings of the breast is limited to the unavoidable minimum.

n a preferred embodiment of the invention, the surroundings of the sub-area are as black in the x-ray image. Evaluation of the x-ray image is thereby made easier and the diagnostically usable structures are more easily recognizable to the eye.

A motorized adjustable collimator device preferably is used for delimitation (definition) of the x-ray beam. This enables a remotely-controllable and automated adjustment of the size and position of the partial beam that is used.

The above object also is achieved in accordance with the present invention by an apparatus having an evaluation device for automatically evaluating the image data transferred from an image transducer in the aforementioned first time segment, and that detects the position and size of the breast, and having a control unit for automatically controlling the collimator using the evaluation result from the evaluation device, in accordance with the method described above.

In an embodiment, an evaluation device is provided that automatically evaluates the image data transferred from the image transducer in the first time segment and detects the position and size of the breast. Moreover, a control device is provided for automatic control of the collimator using the evaluation results determined by the evaluation device. This enables a fast and precise adjustment of the partial beam without time-intensive intervention of the operating personnel being necessary for this purpose.

DESCRIPTION OF THE PREFERRED EMBODIMENTS

Figure 1:
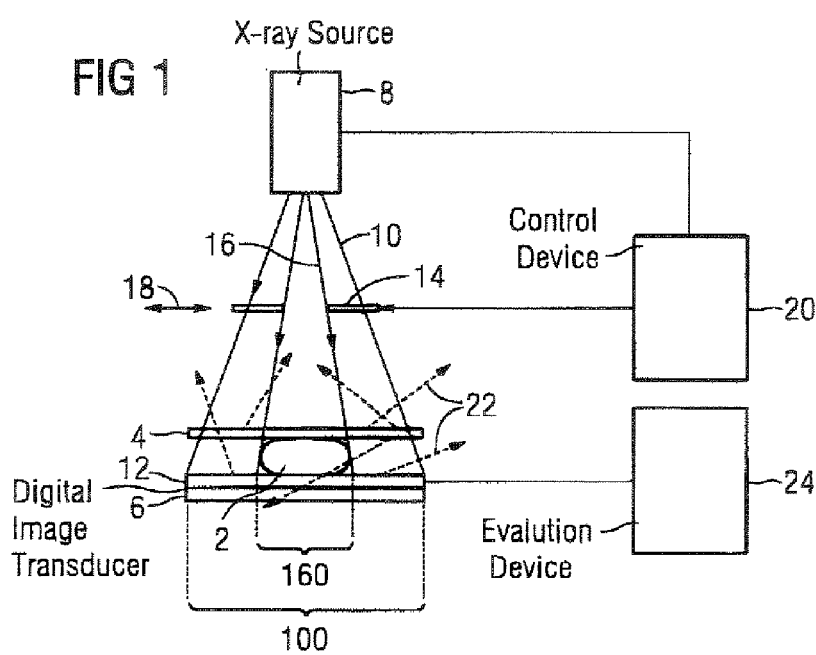
FIG. 1 is a schematic illustration of the basic components at an apparatus according to the invention.

According to FIG. 1, in an apparatus according to the invention the female breast 2 to be examined is disposed between an upper compression plate 4 and a lower compression plate 6. An x-ray source 8 that generates an approximately conical x-ray beam 10 is located above the upper compression plate 4. The upper compression plate 4 facing the x-ray source 8 is transparent for x-ray radiation. An x-ray receiver is arranged on the lower compression plate 6. Serving as an x-ray receiver is a digital image transducer 12 that converts the incident x-ray quanta into a digital image that can be reproduced, for example, on a monitor.

A collimator 14 with which the position and cross-section of a partial beam 16 of the x-ray beam 10 impinging on the upper compression plate can be adjusted is disposed in the beam path of the x-ray beam 10. This is symbolically illustrated in the example by the double arrow 18. For this purpose, the collimator 14 can be adjusted by motors. The position and dimension of the partial beam 16 is controlled by a control device 20. A simple diaphragm whose horizontal position and diaphragm opening are variable is symbolically shown in FIG. 1 as a collimator 14.

In FIG. 1, a situation is shown in which the collimator 14 delimits the x-ray beam 10 to such a degree that just the breast is completely imaged, and the diagnostically uninteresting zones outside of the breast exhibit an optimally small area. In this manner, the scatter radiation 22 (indicated dashed in FIG. 1) that would occur without the presence of a collimator 14 are prevented, and correspondingly the radiation exposure of other body parts of the patient, as well as of the operating personnel, is reduced.

The image acquisition begins in a first time segment with a maximally-opened collimator 14. In the initial position, the entire reception surface 100 of the x-ray receiver 12 is exposed. The x-ray image thereby established, i.e. the image data determined by the digital image transducer, is transferred to an evaluation device 24 connected to the x-ray receiver 12 and there is automatically analyzed, and the position and dimensions of the breast 2 are determined on the reception surface 100. As soon as the position and dimensions of the breast 2 are determined in the x-ray image using the x-ray image created in this first time segment, a sub-area 160 (of the reception area 100) to be exposed is established. Using the evaluation results determined by the evaluation device 24 given the image data analysis and showing the position and size of the sub-area 160, the collimator 14 is adjusted by motors by the control device 20 such that the x-ray beam 10 is limited to the partial beam 16 that exposes only this sub-area 160. In this manner, in a second time segment subsequent to the first time segment only the breast 2 and its immediate surroundings are furthermore exposed to an x-ray radiation necessary for complete image acquisition. Using digital image processing in the evaluation device 24, the surroundings of the breast 2 no longer exposed after the delimitation of the x-ray beam 10 and lying outside of the sub-area 160 are reproduced in black for the image reproduction, such that the completed x-ray image exists in a high-contrast form familiar to the radiologist.

Figure 2A:
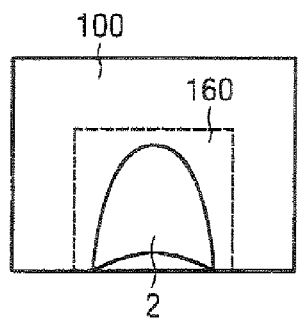
FIGS. 2a, 2b and 2c respectively schematically illustrate x-ray images acquired with the method according to the invention.
Figure 2B:
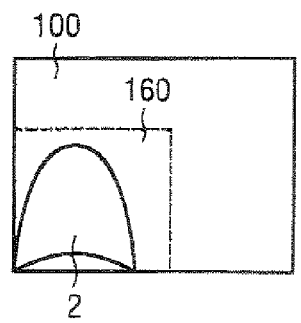
Figure 2C:
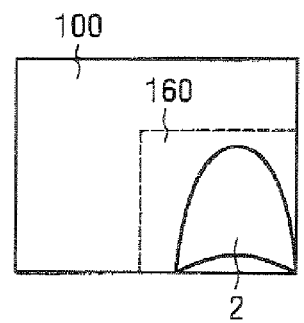

For different positions of the breast 2 on the reception area 100, FIGS. 2a through 2c show respectively different positions of the sub-area 160 exposed in the second time segment after the adjustment of the collimator. The irradiation in the first time segment thereby ensues only until the position of the breast 2 and the size of the image field 160 necessary for the diagnostic can be automatically established on the x-ray image with the aid of the image evaluation device. The ultimate exposure up to an x-ray image that can be diagnostically evaluated then ensues only in the sub-area 160.

In the examples, a rectangular sub-area 160 is shown that is the same size in all three cases. The sub-area 160 can also exhibit a different shape, whereby its shape and size as well as its variability are determined by the collimator used. The sub-area 160 also does not have to encompass the entire breast 2. Rather, it can be sufficient for the sub-area 160 to cover a diagnostically-interesting part of the breast 2.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating an image of a female breast comprising the steps of:
    irradiating a female breast with an x-ray beam and detecting x-rays attenuated by the female breast with a digital image transducer;
    in a first time segment during irradiation of said female breast, irradiating an entirety of a radiation reception area of said digital image transducer with said x-ray beam;
    determining an earliest point in time during irradiation of said female breast with said x-ray beam at which a position and a size of the female breast are detectable in an x-ray image of said female breast produced from an output of said digital image transducer, said point in time ending said first time segment without generation of a diagnostic image of the female breast; and
    in a second time segment during irradiation of said female breast with said x-ray beam, starting at said point in time, limiting said x-ray beam to a partial beam and irradiating only a portion of said radiation reception area of said digital image transducer, or irradiating only a part of said female breast with said partial beam, and completing imaging to generate a diagnostic image of said female breast exclusively using said partial beam.

2. A method as claimed in claim 1 comprising reproducing surroundings of said partial area, outside of said female breast, as black in said x-ray image.

3. A method as claimed in claim 1 comprising passing said x-ray beam through a collimator, and adjusting said collimator to limit said x-ray beam to generate said partial beam.

4. A method as claimed in claim 3 comprising adjusting said collimator with motors in driving connection with movable elements of said collimator.

5. An apparatus for generating an image of a female breast comprising:
    an x-ray source for irradiating a female breast with an x-ray beam;
    a digital image transducer for detecting x-rays attenuated by the female breast;
    a collimator disposed in a path of said x-ray beam, said collimator having movable elements positioned, in a first time segment during irradiation of said female breast, for irradiating an entirety of a radiation reception area of said digital image transducer with said x-ray beam; and
    the first occurance of an evaluation device connected to said digital image transducer configured to determine, in a second time segment an earliest point in time during irradiation of said female breast with said x-ray beam at which a position and a size of the female breast are detectable in an x-ray image of said female breast produced from an output of said digital image transducer, said point in time ending said first time segment without generation of a diagnostic image of the female breast, and a control unit provided with a signal from said evaluation unit at said point in time configured to changed; said movable elements in position to limit said x-ray beam to a partial beam for irradiating only a portion of said radiation reception area of said digital image transducer, or irradiating only a part of said female breast with said partial beam, with imaging of said female breast being completed to generate a diagnostic image exclusively using said partial beam.

6. An apparatus as claimed in claim 5 comprising an image processor that reproduces surroundings of said partial area, outside of said female breast, as black in said x-ray image.

7. An apparatus as claimed in claim 5 comprising at least one motor in driving connection with movable elements of said collimator for adjusting said movable elements to limit said x-ray beam.

8. An apparatus as claimed in claim 5 comprising said evaluation unit connected to said digital image transducer that automatically electronically identifies said point in time, and said control unit connected to said motor and to said evaluation unit for operating said motor to limit said x-ray beam upon triggering by said evaluation unit at said point in time.

* * * * *